United States Patent
Zhang et al.

(10) Patent No.: US 8,538,111 B2
(45) Date of Patent: Sep. 17, 2013

(54) METHOD AND APPARATUS FOR PULMONARY VENTILATION IMAGING USING LOCAL VOLUME CHANGES

(75) Inventors: Geoffrey G. Zhang, Tampa, FL (US); Kenneth M. Forster, Dallas, TX (US)

(73) Assignee: University of South Florida, Tampa, FL (US)

( * ) Notice: Subject to any disclaimer, the term of this patent is extended or adjusted under 35 U.S.C. 154(b) by 248 days.

(21) Appl. No.: 12/988,773

(22) PCT Filed: Apr. 21, 2009

(86) PCT No.: PCT/US2009/041252
§ 371 (c)(1),
(2), (4) Date: Oct. 20, 2010

(87) PCT Pub. No.: WO2009/132002
PCT Pub. Date: Oct. 29, 2009

(65) Prior Publication Data
US 2011/0058721 A1    Mar. 10, 2011

Related U.S. Application Data

(60) Provisional application No. 61/046,605, filed on Apr. 21, 2008, provisional application No. 61/058,023, filed on Jun. 2, 2008.

(51) Int. Cl.
*G06K 9/00* (2006.01)
(52) U.S. Cl.
USPC ........................................... 382/131
(58) Field of Classification Search
None
See application file for complete search history.

(56) References Cited

U.S. PATENT DOCUMENTS

| | | | |
|---|---|---|---|
| 6,407,738 B1 | 6/2002 | Wakabayashi | |
| 2006/0072821 A1* | 4/2006 | Wang | 382/173 |
| 2008/0009760 A1* | 1/2008 | Wibowo et al. | 600/529 |

OTHER PUBLICATIONS

Guerrero, T., et al., "Dynamic Ventilation Imaging From Four-Dimensional Computed Tomography," 2006, Physics in Medicine and Biology, vol. 51, No. 4, pp. 1-16.*
Bourdin, X, et al, Comparison of tetrahedral and hexahedral meshes for organ finite element modelling: an application to kidney impact, Jun. 2007, 20th Enhanced safety of vehicles conference: innovations for safety: opportunities and challenges, pp. 1-10.*
Wiemker, Rafael, et al, Computer Aided Lund Nodule Detection on High Resolution CT Data, 2002, Proceedings of SPIE, vol. 4684, pp. 1-12.*

(Continued)

*Primary Examiner* — Utpal Shah
(74) *Attorney, Agent, or Firm* — Saliwanchik, Lloyd & Eisenschenk

(57) ABSTRACT

The invention provides a novel method of high-resolution quantifiable pulmonary regional ventilation imaging using a package of computer programs, including deformable image registration and local volume change calculation on 4-D or breath-hold CT images. High resolution 3D ventilation images have been generated using this technique with superior quality. The deformation matrices between different respiration phases are calculated using deformable image registration and applied to calculate local volume change ΔV between respiration phases. The invention provides less image-noise and mismatch sensitivity than other techniques based on CT images, and is less expensive than nuclear medicine imaging. Implemented clinically, the method can derive a patient's pulmonary ventilation information from the same set of 4-D CT images, providing a cheaper but more accurate method to generate clinical lung ventilation image. Such information can be utilized in treatment planning sparing functional lung volumes without additional procedure and cost for lung functional imaging.

25 Claims, 10 Drawing Sheets

(56) References Cited

OTHER PUBLICATIONS

Reduction to Repeated Integrals, http://poncelet.math.nthu.edu.tw/disk3/cal03/html/3-int/3-int.html, last modified Feb. 25, 2003 (see p. 2), pp. 1-2.*

Math Forum—Ask Dr. Math: Volume of a Tetrahedron, Jan. 2002 (see p. 1), The Math Forum—Ask Dr. Math (http://mathforum.org/library/drmath/view/51837.html), pp. 1-3.*

Min, Chohong, et al, Geometric integration over irregular domains with application to level-set methods, Jun. 2007, Journal of Computational Physics, vol. 226, pp. 1-12.*

Beauchemin, S.S., et al., "The Computation of Optical Flow," *ACM Computing Surveys*, 1995, pp. 433-466, vol. 27, No. 3.

Bunow, B., et al., "Regional Ventilatory Clearance by Xenon Scintigraphy: A Critical Evaluation of Two Estimation Procedures," *Journal of Nuclear Medicine*, 1979, pp. 703-710, vol. 20, No. 7.

Gottschalk, A., et al., "Ventilation-Perfusion Scintigraphy in the PIOPED Study, Part II: Evaluation of the Scintigraphic Criteria and Interpretations," *Journal of Nuclear Medicine*, 1993, pp. 1119-1126, vol. 34, No. 7.

Guerrero, T., et al., "Dynamic Ventilation Imaging From Four-Dimensional Computed Tomography," *Physics in Medicine and Biology*, 2006, pp. 777-791, vol. 51, No. 4.

Guerrero, T., et al., "Intrathoracic Tumour Motion Estimation from CT Imaging Using the 3D Optical Flow Method," *Physics in Medicine and Biology*, 2004, pp. 4147-4161, vol. 49, No. 17.

Guerrero, T., et al., "Quantification of Regional Ventilation from Treatment Planning CT," *International Journal of Radiation Oncology, Biology, Physics*, 2005, pp. 630-634, vol. 62, No. 3.

Harris, B., et al., "Objective Analysis of Tomographic Ventilation-Perfusion Scintigraphy in Pulmonary Embolism," *American Journal of Respiratory and Critical Care Medicine*, 2007, pp. 1173-1180, vol. 175, No. 11.

Horn, B.K.P., "Determining Optical Flow," *Artificial Intelligence*, 1981, pp. 185-203, vol. 17, No. 1-3.

Huang, T.C., "Semi-Automated CT Segmentation Using Optic Flow and Fourier Interpolation Techniques," *Computer Methods and Programs in Biomedicine*, 2006, pp. 124-134, vol. 84, No. 2-3.

Lavrenkov, K., et al., "A Potential to Reduce Pulmonary Toxicity: The Use of Perfusion SPECT with IMRT for Functional Lung Avoidance in Radiotherapy of Non-Small Cell Lung Cancer," *Radiotherapy and Oncology*, 2007, pp. 156-162, vol. 83, No. 2.

Levin, D.L., "Evaluation of Regional Pulmonary Perfusion Using Ultrafast Magnetic Resonance Imaging," *Magnetic Resonance in Medicine*, 2001, pp. 166-171, vol. 36, No. 1.

Liu, H., et al., "Accuracy vs. Efficiency Trade-offs in Optical Flow Algorithms," *Computer Vision and Image Understanding*, 1998, pp. 271-286, vol. 72, No. 3.

Marcucci, C., "Distribution of Pulmonary Ventilation Using Xe-Enhanced Computed Tomography in Prone and Supine Dogs," *Journal of Applied Physiology*, 2001, pp. 421-430, vol. 90, No. 2.

Melo, M.F.V., et al., "Quantification of Regional Ventilation-Perfusion Ratios with PET," *Journal of Nuclear Medicine*, 2003, pp. 1982-1991, vol. 44, No. 12.

Nakagawa, T., "Pulmonary Ventilation-Perfusion MR Imaging in Clinical Patients," *Journal of Magnetic Resonance Imaging*, 2001, pp. 419-424, vol. 14, No. 4.

Petersson, J., "Physiological Evaluation of a New Quantitative SPECT Method Measuring Regional Ventilation and Perfusion," *Journal of Applied Physiology*, 2004, pp. 1127-1136, vol. 96, No. 3.

Shioyama, Y., et al., "Preserving Functional Lung Using Perfusion Imaging and Intensity-Modulated Radiation Therapy for Advanced-Stage Non-Small Cell Lung Cancer," *International Journal of Radiation Oncology, Biology, Physics*, 2007, pp. 1349-1358, vol. 83, No. 5.

Simon, B.A., "Non-Invasive Imaging of Regional Lung Function Using X-Ray Computed Tomography," *Journal of Clinical Monitoring and Computing*, 2000, pp. 433-442, vol. 16, No. 1.

Suga, K., "Altered Clearance of Gadolinium Diethylenetriaminepentaacetic Acid Aerosol from Bleomycin-Injured Dog Lungs," *American Journal of Respiratory and Critical Care Medicine*, 2003, pp. 1704-1710, vol. 167, No. 12.

Willey-Courand, D.B., "Alterations in Regional Ventilation, Perfusion, and Shunt After Smoke Inhalation Measured by PET," *Journal of Applied Physiology*, 2002, pp. 1115-1122, vol. 93, No. 3.

Zhang, G.G., et al., "Dose Mapping: Validation in 4D Dosimetry with Measurements and Application in Radiotherapy Follow-Up Evaluation," *Computer Methods and Programs in Biomedicine*, 2008, pp. 25-37, vol. 90, No. 1.

Zhang, G., et al., "Use of Three-Dimensional (3D) Optical Flow Method in Mapping 3D Anatomic Structure and Tumor Contours Across Four-Dimensional Computed Tomography Data," Journal of Applied Clinical Medical Physics, 2008, pp. 59-69, vol. 9, No. 1.

* cited by examiner image 1 image 2

METHOD AND APPARATUS FOR PULMONARY VENTILATION IMAGING USING LOCAL VOLUME CHANGES

CROSS-REFERENCE TO RELATED APPLICATIONS

The present application is the U.S. National Stage Application of International Patent Application No. PCT/US2009/041252, filed on Apr. 21, 2009, which claims the benefit of U.S. Provisional Application Ser. No. 61/046,605, filed Apr. 21, 2008, and claims the benefit of U.S. Provisional Application Ser. No. 61/058,023, filed Jun. 2, 2008, all of which are hereby incorporated by reference herein in their entirety, including any figures, tables, or drawings.

BACKGROUND OF THE INVENTION

Pulmonary ventilation and perfusion typically vary when pulmonary diseases are involved. (Nakagawa T, et al., *J Magnetic Resonance Imaging* 2001; 14:419-424). However, in current practice of thoracic cancer radiotherapy, the differences in pulmonary ventilation and perfusion are not considered when generating treatment plans. Lung volumes are deemed equal when placing radiation beams in planning. Clinicians and researchers have proposed to include normal lung sparing in thoracic cancer radiotherapy by introducing ventilation or perfusion imaging into radiotherapy treatment planning. (Lavrenkov K, et al., *Radiother Oncol* 2007; 83:156-162; Shioyama Y, et al., *Int J Radiat Oncol Biol Phys* 2007; 68:1349-1358) If clinically implemented, introducing ventilation or perfusion imaging into radiotherapy treatment planning may reduce radiation toxicity to the lungs while still providing adequate radiation dose coverage to the tumors.

Different imaging modalities are currently used clinically for pulmonary ventilation evaluation. Nuclear medicine, including nuclear scintigraphy (Bunow B, et al., *J Nucl Med* 1979; 20:703-710; Gottschalk A, et al., *J Nucl Med* 1993; 34:1119-1126), single photon emission computed tomography (SPECT) (Harris B, et al., *Am I Resp Crit Care Med* 2007; 175:1173-1180; Petersson J, et al., *J Appl Phisiol* 2004; 96:1127-1136), and positron emission tomography (PET) (Melo M, et al., *J Nucl Med* 2003; 44:1982-1991; Willey-Courand D B, et al., *J Appl Phisiol* 2002; 93:1115-1122), is the most commonly used modality. Magnetic resonance imaging (MRI) (Levin DL, et al., *Magn Reson Med* 2001; 46:166-171; Suga K, et al., *Am J Respir Crit Care Med* 2003; 167:1704-1710) and computed tomography (CT) (Marcucci C, et al., *J Appl Phisiol* 2001; 90:421-430; Simon B A., *J Clin Monitoring Computing* 2000; 16:433-442) are also capable of pulmonary functional imaging.

The intrinsic spatial resolution of the gamma cameras used in scintigraphy and SPECT is determined by the quantum detection efficiency, the thickness of the NaI(TI) crystal, the size of photomultiplier tube (PMT), the size of the collimator holes, the thickness of the collimator, and the energy of the incident photons. The typical intrinsic spatial resolution for modern scintillation cameras with crystals of ⅜ inch thickness is about 4 mm using with $^{99m}Tc$ radionuclide.

The spatial resolution of modem PET can be better than 5 mm in the center of the detector ring. Off-center spatial resolution is slightly worse. The factors that primarily affect the spatial resolution include (1) the intrinsic spatial resolution of the detectors which is mainly determined by the size of the individual scintillation crystal; and (2) the distance that the emitted positrons travel before annihilation, which is determined by the maximum positron energy of the radionuclide and the density of the tissue. The intrinsic spatial resolution of the detectors is the major limit of the spatial resolution of a PET system.

The higher spatial resolution is the advantage of MRI and CT over nuclear medicine. There are many techniques in MRI ventilation studies. The most common approach of MRI based pulmonary ventilation assessment uses gadolinium-based contrast agents. Due to the complexity of MRI based ventilation imaging, the clinical application of this technique is not common. Traditionally, iodine-based radiocontrast agents are used in CT based ventilation imaging.

Recently, Guerrero, et al. (Guerrero T, et al., *Phys Med Biol* 2006; 51:777-791; Guerrero T, et al., *Int J Radiat Oncol Biol Phys* 2005; 62:630-634) reported a method of ventilation imaging using 4-D CT, using no radiocontrast agents. The Hounsfield unit (HU) change was involved in the ventilation calculation. Deformable image registration was applied between respiratory phases of 4-D CT images. The deformation matrices calculated from the registration were used to link voxels in one phase and the corresponding voxels in the other phase. The HU differences between the corresponding voxels of the two phases were used in the ventilation calculation.

The advantages of ventilation imaging using 4-D CT data include: (1) 4-D CT is a mature technology and is commercially available; (2) no additional procedure such as contrast inhalation is needed, which makes the clinical implementation straightforward; (3) high spatial resolution of lung functional imaging can be achieved, which is a major advantage over nuclear medicine; (4) 4-D CT is a much less expensive procedure than other imaging modalities (it would be a great cost relief for clinical ventilation imaging); and (5) since 4-D CT is become routine for thoracic cancer radiation therapy planning, no additional procedure, such as a nuclear medicine or MRI imaging session, is needed for ventilation imaging. This reduces the cost and time for the radiotherapy patient.

The problem related to the HU change method is that the fluctuation of the HU in a CT image makes the ventilation image noisy and affects the HU-based ventilation images directly. The other problem with this method is the edge artifact. The mismatched regions on the low-high density interface, such as the interface between the lung tissues and blood vessels, and between the lung and chest wall, cause artifact of high ventilation spikes. This is because the voxel-to-voxel ratio of the intensity is used in the ventilation images, which magnifies the noise in CT images. Usually, a number of voxels are averaged for ventilation calculation using this method to smoothen the noise. This would make the spatial resolution of ventilation images coarser, losing the advantage of CT images over nuclear medicine ventilation images. The partial volume effect in CT images makes the CT voxel intensity higher or lower, which in turn creates artifact in the ventilation images.

Any voxel-to-voxel mismatch at the edge of high-low intensity interface, such as blood vessels and lung tissue interface, chest wall and lung interface, would cause spikes in ventilation images. The mismatched edges can be seen in FIG. 6. Even with averaging technique, these spikes would still introduce false high ventilation volumes.

BRIEF SUMMARY

Embodiments of the subject invention relate to a method and apparatus for ventilation imaging. In a specific embodiment, a method and apparatus for use in ventilation computed tomography (CT) imaging is provided. The ventilation calculation used in specific embodiments of the present invention uses the local volume change directly. Specific embodiments also incorporate deformable image registration.

In accordance with embodiments of the subject invention voxel-to-voxel deformation matrices between different respiration phases are calculated using deformable image registration. The matrices are then applied to calculate local volume change $\Delta V$ between respiration phases for each voxel. A three-dimensional (3-D) high-resolution pulmonary regional ventilation image, defined as $\Delta V/V$ for every voxel, is then generated. The change of a local volume, represented by a polyhedron, can be calculated by summing changes of multiple tetrahedrons that form in the polyhedron.

BRIEF DESCRIPTION OF DRAWINGS

For a fuller understanding of the invention, reference should be made to the following detailed description, taken in connection with the accompanying drawings, in which.

DETAILED DISCLOSURE

Figure 1:
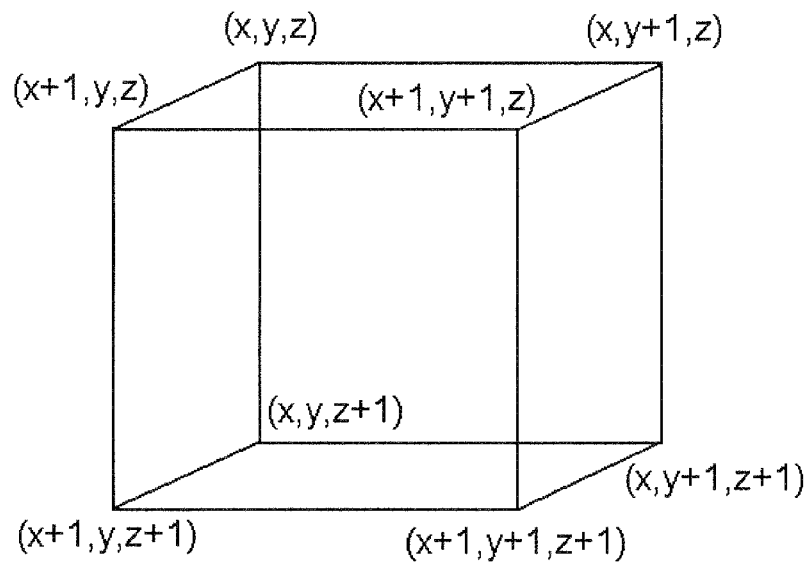
FIG. 1 shows how a cuboid representing the voxel (x,y,z) in image 1 changes to a 12-face polyhedron in image 2, where both the cuboid and the 12-face polyhedron have 8 vertexes.
Figure 1:
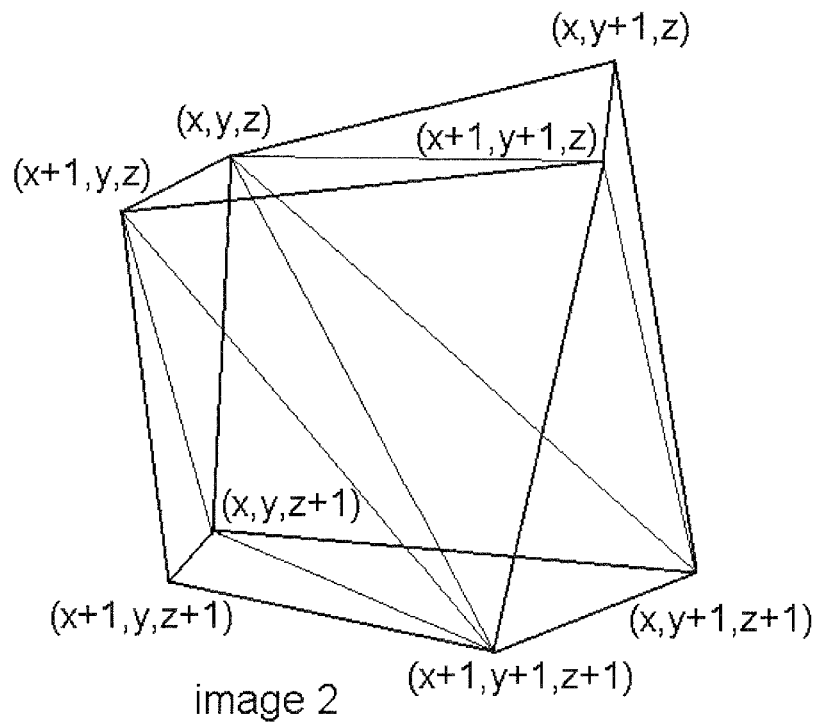

Embodiments of the subject invention relate to a method and apparatus for ventilation imaging. In a specific embodiment, a method and apparatus for use in ventilation computed tomography (CT) imaging is provided. Specific embodiments pertain to a method and apparatus for high resolution pulmonary ventilation imaging by using deformable image registration and local volume change to calculate ventilation. Since 4-D CT is less expensive than nuclear medicine, including SPECT and PET, and easier to perform, certain implementations of pulmonary ventilation imaging using nuclear medicine can be replaced by an embodiment of the subject invention using 4-D CT, unless concurrent perfusion imaging is required. Embodiments of the invention using 4-D CT can be used in radiological studies for pulmonary fibrosis, emphysema, or other indications of reduced lung function.

In lung cancer radiotherapy, 4-D CT images are often used to assess lung tumor motion. Using embodiments of the subject method clinically, the same set of CT images can also be used to obtain the patient's pulmonary ventilation information, which can be utilized in treatment planning to spare normal functional lung volumes without additional imaging procedures or additional cost. Embodiments of the subject method can also provide a practical method for post therapy evaluation for radiation and chemo patients of thoracic cancers. In a specific embodiment, a ventilation image from before therapy can be compared to a ventilation image from after therapy, or treatment to gauge how effective therapy or treatment was.

The voxel-to-voxel deformation matrices between CT images of different respiration phases can be calculated by deformable image registration. The matrices can then be used to calculate local volume change $\Delta V$ for each voxel. A 3-D high resolution pulmonary ventilation image can then be generated by directly calculating $\Delta V/V$ for every voxel.

In an experiment using an embodiment of the invention ventilation calculations were performed on 12 of the patients. The 4-D CT images were taken using a 16-slice Brillance Big Bore CT scanner (Philips Medical Systems, Cleveland, Ohio). An air bellows belt with a pressure transducer was wrapped around the abdomen. The bellows belts converted the pressure waveform into respiratory phase information (Philips Medical Systems), which was used for 4-D data tagging. The 4-D sinograms were sorted using amplitude mode and then reconstructed for each individual phase. The pixel size in the transaxial slice of the 4-D CT images was approximately 0.98×0.98 mm$^2$, and the slice thickness was 3 mm. Accordingly, the volume of each voxel was 2.88 mm$^3$. A complete set of 3-D CT images was reconstructed for each respiratory phase from the 4-D binned data. The 4-D CT image sets were acquired and reconstructed for 10 respiratory phases yielding 10 complete sets of 3-D CT images across the whole respiratory cycle. The 10 respiratory phases were labeled as 0%, 10%, . . . , 90% phases, with 0% phase corresponding to normal end inspiration and 50% to end expiration.

Deformable image registration was used to generate voxel-to-voxel deformation matrices among the involved CT image sets. The deformable image registration application used in this embodiment called optical flow, is image intensity gradient-based. This application was originally developed for 2-D image registrations. (Horn B, Schunck B, *Artif Intell* 1981; 17:185-203; Huang T, et al., *Comp Meth Prog in Biomed* 2006; 84:124-134). A 3-D optical flow program was developed to handle 4-D problems, such as calculating the deformation between respiratory phased in a 4-D CT data set. (Zhang G, et al., *Comp Meth Prog in Biomed* 2008; 90:25-37).

In the CT image, each voxel can be represented by as set of vertices. In a specific embodiment, each voxel can be represented by a cuboid. As shown in FIG. 1, the 8 vertices that define the cuboid for voxel (x,y,z) in image 1 can be changed to create a 12-face polyhedron as shown in image 2. These 8 vetices define the same local volume in a body but with different shapes and sizes in the two image sets of different respiratory phases. The polyhedron in image 2 is still made up of the 8 corresponding vertices. Deformable image registration establishes the correspondence of the vertices. In the local volume change calculation step, the volume of each voxel is calculated using the corresponding vertices of each respective polyhedron.

Figure 2:
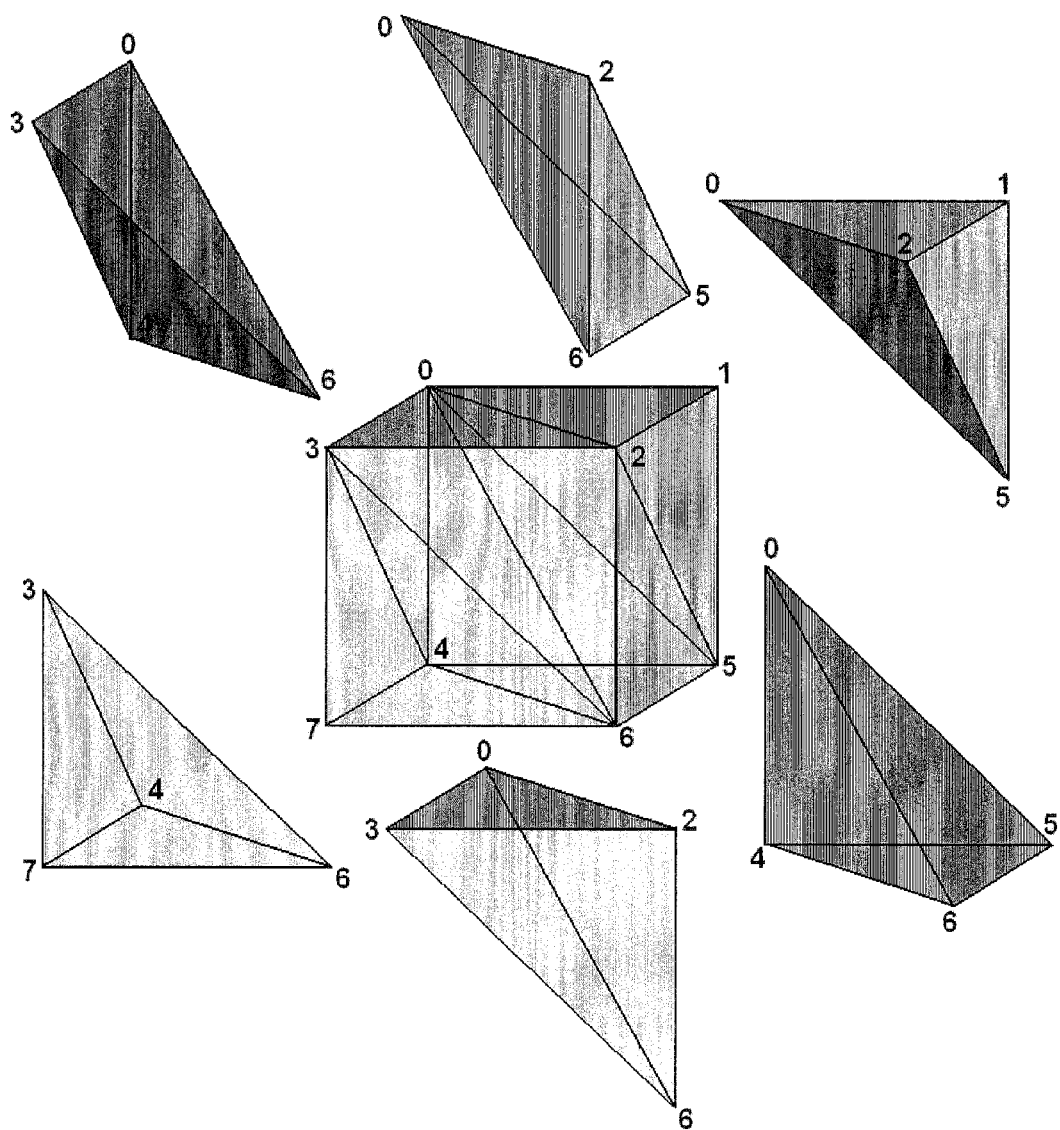
FIG. 2 shows a cuboid divided into 6 tetrahedrons, where the vertex numbers are shown on the cuboid and the tetrahedrons correspondingly.
Figure 3:
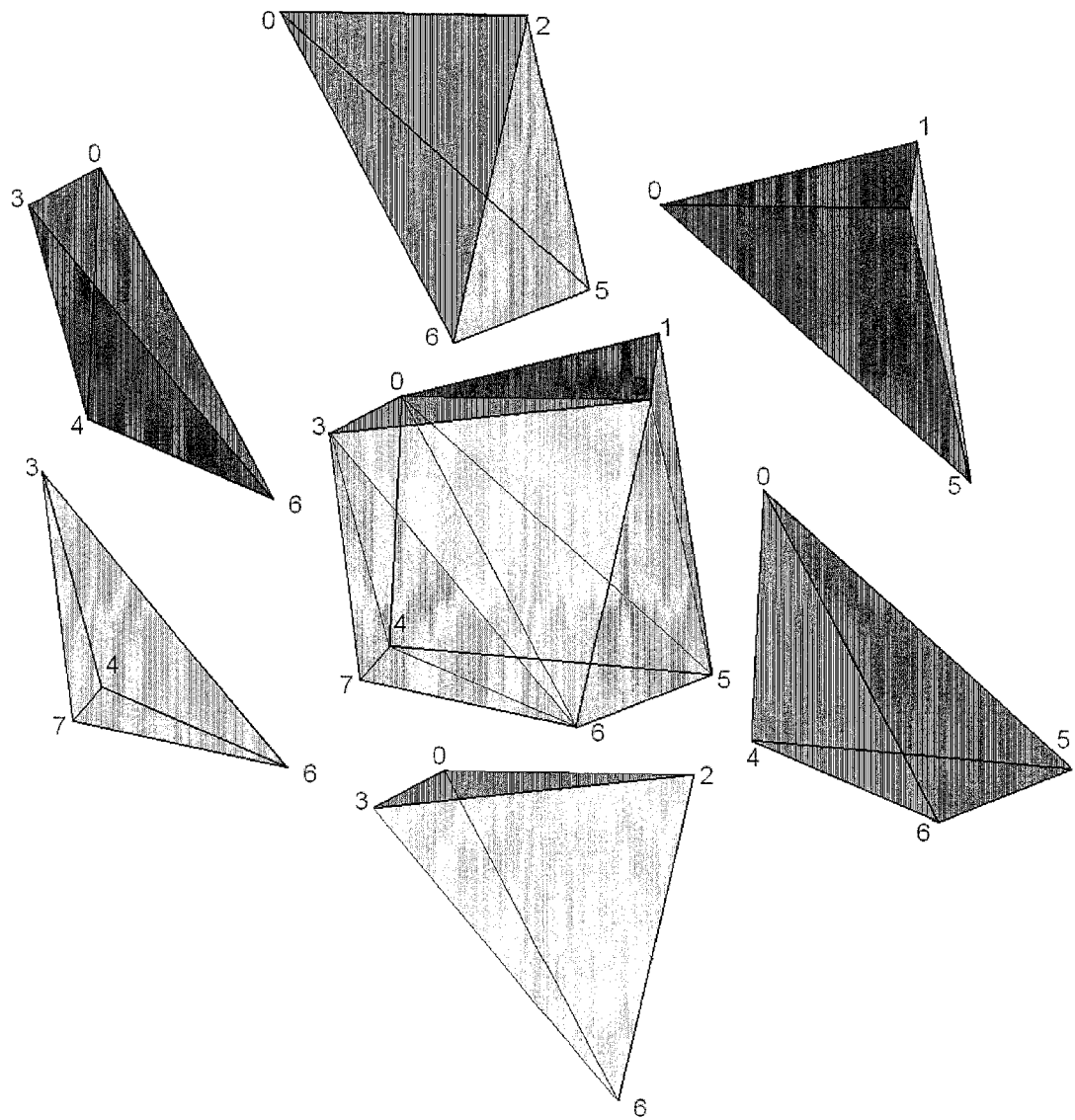
FIG. 3 shows a deformed cuboid is a 12-face polyhedron that is composed of the 6 deformed tetrahedrons, where the vertex numbers are shown on the cuboid and the tetrahedrons correspondingly.

Any hexahedron can be divided into 6 tetrahedrons. The cuboid in image 1 of FIG. 1 was divided into 6 tetrahedrons, as shown in FIG. 2. The deformed cuboid is a polyhedron of up to 12 faces, which can be broken into the 6 deformed tetrahedrons shown in FIG. 3. The volumes of the cuboid and the deformed cuboid are the sums of the volumes of the 6 corresponding tetrahedrons, respectively.

The fundamental volume calculation part in the program is the calculation of the volume of a tetrahedron. The coordinates of the 4 vertexes of a tetrahedron can be used to determine the volume, using:

$$V=(b-a)\cdot[(c-a)\times(d-a)]/6 \quad (1)$$

where a, b, c, d are the vertices as vectors. The volumes of the six tetrahedrons are added to generate the volume of the give polyhedron. The coordinates of the deformed tetrahedron can be calculated from the deformation matrix that results from the deformable image registration.

The volume calculation program can also allow user-defined numbers of voxels to be a unit volume. For example, if the user selects 2×2×1 voxels to be a unit volume, the volume change calculation can then be based on each 2×2×1 voxels. This is analogous to the averaging calculation in the HU change technique taught by Guerrero et al.

Pulmonary ventilation P can be defined as the fractional volume change in respiration. In a specific embodiment, P can be expressed mathematically as $$P\ \Delta V/V \quad (2)$$

where V is the local volume at expiration and $\Delta V$ is the volume change from expiration to inspiration. In specific embodiments, the volume change, $\Delta V$, can be determined from any two points in the respiration cycle and the local volume can be the volume at either of the two points, or some value based on the volume of one or both points such as an average of the volumes at the two points. In a specific embodiment utilizing three or more image data sets, a volume change from a first to a second image data set can be calculated and then volume changes from the second to a third, from the third to a fourth, up to from m−1 to $m^{th}$ for m image data sets can be calculated and added together to calculate the volume change from the first to the $m^{th}$ image data set.

Considering two CT image sets, one taken at expiration and the other taken at inspiration, in a specific embodiment the volume of each voxel in expiration can be considered a constant, determined by the CT voxel size. The voxel volume can then be considered to expand during inspiration. The boundary of each voxel in the expiration image set is then deformed and no longer the same as the voxel transitions to the inspiration image set. Deformable image registration can determine the new boundary location of the voxel in the inspiration image set. The volume calculation program can calculate the volume of the deformed voxel. The volume change $\Delta V$ can then be the volume difference between the volume in expiration and the volume in inspiration.

In an embodiment, ventilation calculations can be performed in one of two ways when 4-D CT data are used: (1) 4-D dynamic ventilation series, or (2) expiration-inspiration ventilation. In the calculations for the 4-D dynamic ventilation series, the deformable image registration can be performed in the order of 50%-60%, 50%-70%, 50%-80%, 50%-90%, and 50%-0%. Each of the volume changes from the series can be between the corresponding respiration phase and maximum expiration.

When the deformable image registration is performed on the image pair of 50%-0%, the expiration-inspiration ventilation image set can be generated based on the 50%-0% deformation matrix. Breath-hold CT data was also used to generate expiration-inspiration ventilation. As the deformable image registration provided sub voxel-size displacements in the deformation matrix, small volume change can be calculated, which results in a smooth ventilation image.

The validation of an embodiment of the invention was divided into two parts: validation of deformable image registration and validation of the volume calculation.

The validation of tetrahedron volume calculation was straightforward. The volumes of tetrahedrons of different shapes were calculated using the program and compared with manual calculations. No difference was noted.

The 3-D optical flow program was validated against known displacements, with the mean error of the registration less than the voxel size. (Guerrero T, et al., *Phys Med Biol* 2004; 49:4147-4161). The program was applied in 4-D radiation dose mapping in a lung cancer radiotherapy dosimetry study. The calculated dose was compared with the measurements, with agreement better than 2%. (Zhang G, et al., *Comp Meth Prog in Biamed* 2008; 90:25-37). Detailed error analysis of the use of optical flow with 4-D CT images has been reported elsewhere. (Zhang G, et al., *J Appl Clin Med Phy* 2008; 9:59-69).

As another validation test, the tidal volume from the ventilation calculation was compared with the segmented lungs of maximum inspiration and expiration. The volume changes of all voxels in the lungs were accumulated in the ventilation calculation, for example by integrating the local volume change $\Delta V$ over the entire lung volume. This total volume change should be the tidal volume. Alternatively, the tidal volume was calculated using the maximum expiration and inspiration images from the 4-D CT, where the lungs were segmented using an intensity threshold. Automatic contouring of normal lung using intensity threshold was applied because it is much more consistent than manual contouring. The tidal volume from the segmented lungs was compared with the one from the ventilation calculation. The tidal volume comparison was performed for 15 cases. The maximum difference of all cases was 3% of the segmented tidal volume with most of the cases below 1%. The total volume changes between other respiration phases were also compared between calculating based on ventilation and calculating based on segmentation. A comparison of the volume changes in a series of dynamic ventilation imaging is listed in Table 1.

TABLE 1

Comparison of lung volume change between calculations from ventilation imaging and calculations from lung segmentation using 4-D CT data.

| Phase Pair | ΔV from ventilation (cm³) | ΔV from segmentation (cm³) | % difference |
|---|---|---|---|
| 50%-80% | 120.9 | 121.3 | 0.3% |
| 50%-90% | 224.7 | 224.1 | −0.3% |
| 50%-0% | 291.4 | 289.9 | −0.5% |

Figure 4:
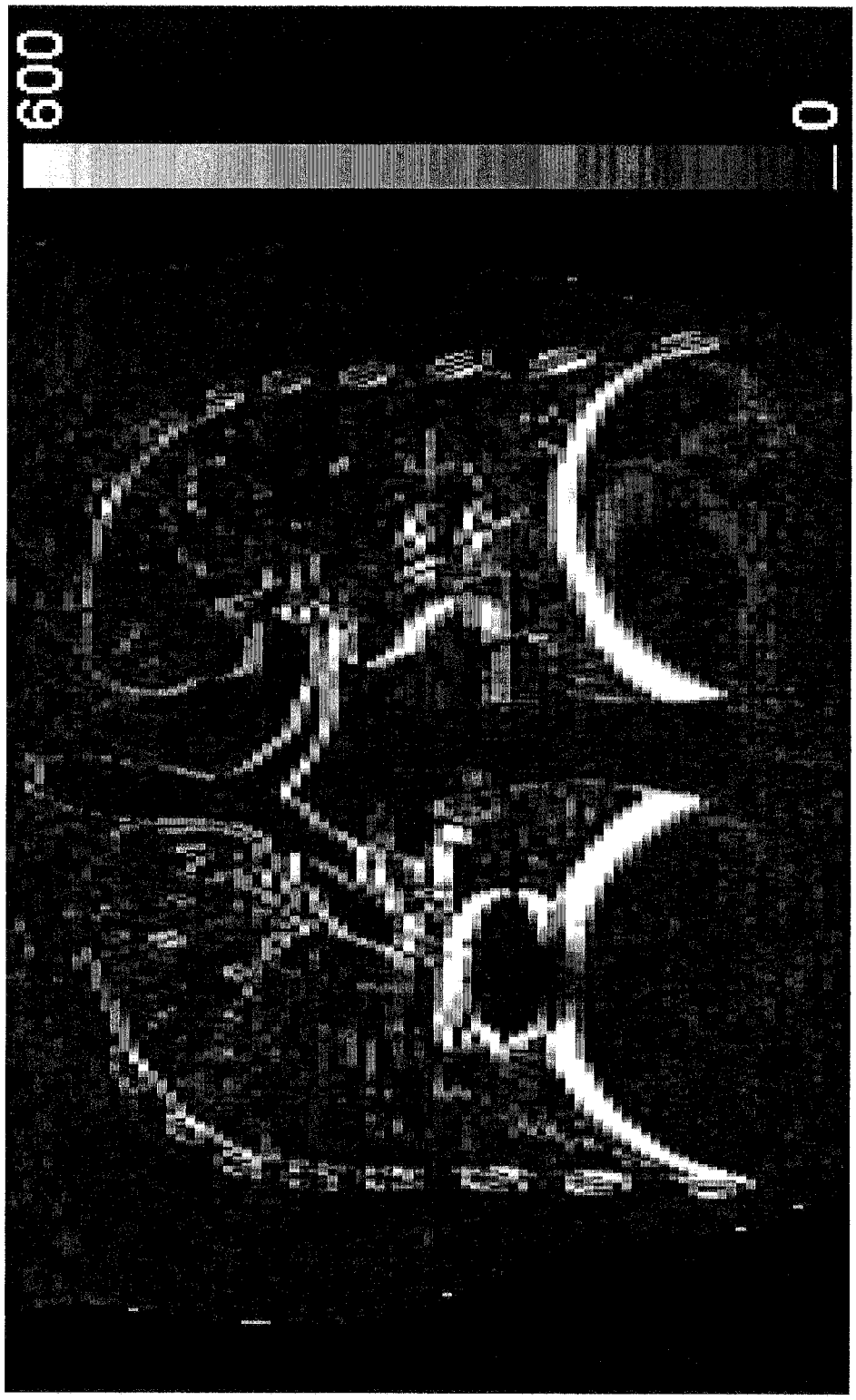
FIG. 4 shows an example of deformable image registration, showing the difference between the images of maximum inspiration and expiration phases, where the grey level of the difference represents the CT number difference as scaled, and absolute values are used in the difference calculation.
Figure 5:
FIG. 5 shows the deformation matrix overlapping with the images of the two phases.
Figure 6:
FIG. 6 shows the difference between the images of maximum expiration and the registered images of inspiration-to-expiration, where only coronal views are shown in this figure.

FIGS. 4-6 show an example of deformable image registration. The end (maximum) inspiration phase (0%) was registered to the end (maximum) expiration phase (50%) from a 4-D CT image set of a lung cancer patient. The differences of before and after registration are shown in FIGS. 4 and 6, respectively. The deformation matrix derived from the inspiration-to-expiration registration is also graphically shown in a coronal view in FIG. 5, where upward motion of the diaphragm can be observed. In FIG. 4, the most prominent difference is caused by the diaphragm motion. A lung tumor is just above the right diaphragm. The tumor motion can also be seen, which causes an obvious difference in FIG. 4. Referring to FIG. 6, compared with FIG. 4, the difference has been significantly minimized.

Figure 7:
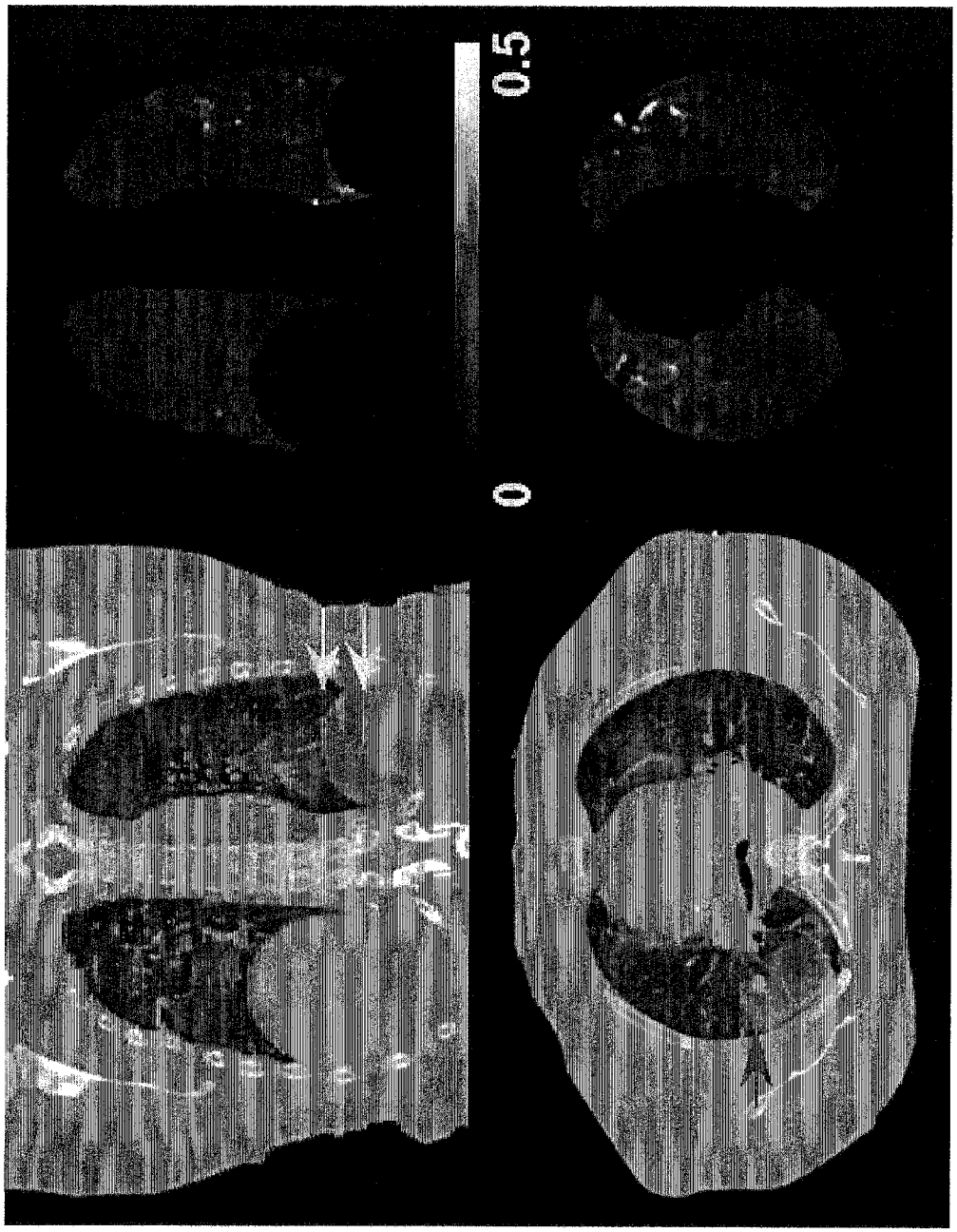
FIG. 7 shows an example of a 50%-0% (expiration-inspiration) ventilation image, where the upper row is a coronal view of overlapping CT images of 50% and 0% phases, and the corresponding ventilation image; and the lower row is a transaxial view of the same CT and ventilation images at the location of a lung tumor (indicated by the red arrow on the CT image).

An example of 50%-0% ventilation image is shown in FIG. 7. In this example, different volume changes between left and right lungs are evidenced by the differing motion of the two hemi-diaphragms in the overlapping coronal CT images taken at the end (maximum) expiration and inspiration phases. The arrows on the CT image set indicate that the diaphragm motion range was large on the left lung side, about 3 cm, while the diaphragm motion the right side was small, about 3 mm. This volume change difference can be observed on the ventilation image. Specifically, the ventilation difference of the left and right lungs is shown in the corresponding ventilation image (upper row in FIG. 7). Lower ventilation around lung tumor region was also observed in the ventilation image in the lower row of FIG. 7. These later images also suggest greater regional ventilation of the anterior segments of lung when compared to the posterior ones. The ventilation image is scaled as ΔV/V=0 as black and 1 as white.

Figure 8:
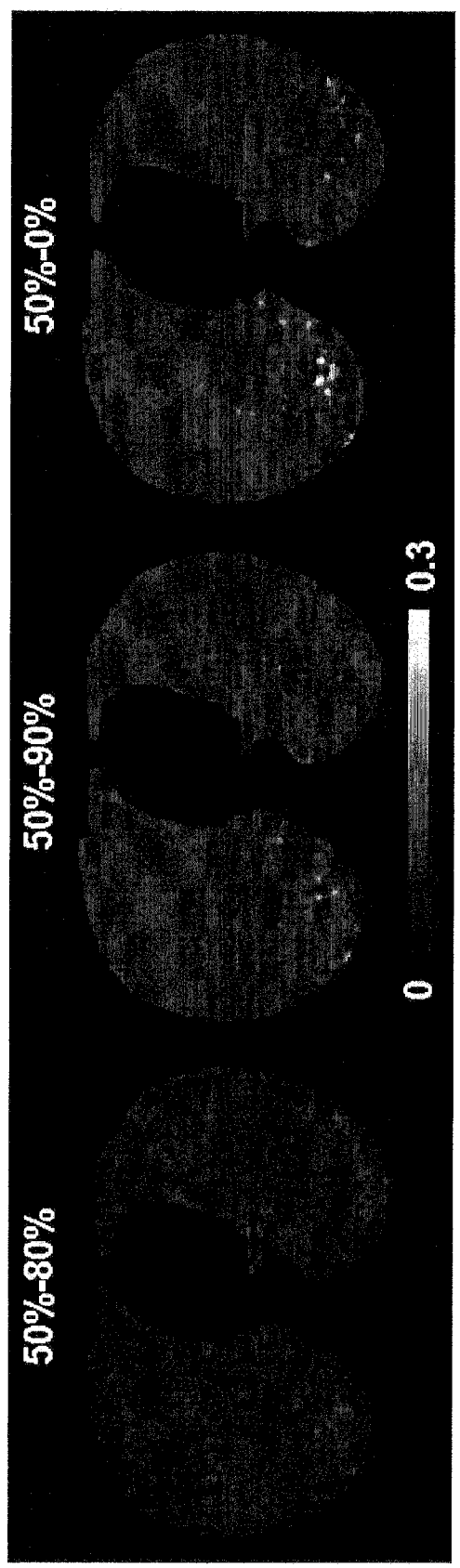
FIG. 8 shows transaxial views of a series of integral dynamic ventilation images produced in accordance with an embodiment of the invention, where the upper panel shows the ventilation image of 50% phase to 80% phase with a total lung volume increase of 120.9 cm$^3$; the middle panel is the ventilation image of 50% to 90% with a total lung volume change of 224.7 cm$^3$; the lower panel is the maximum integral ventilation image of 50% to 0% phases with a corresponding total lung volume change of 291.4 cm$^3$, where the brightness of all the images were scaled from $\Delta V/V=0$ (black) to 1 (white).

A series of integral, or accumulative, dynamic ventilation images is shown in FIG. 8, depicting the accumulation effect in this series as data from additional phases of respiration are incorporated. The total lung volume change, an integral of ΔV for each ventilation image set, was compared with the change calculated from automatic lung segmentation of corresponding phases of CT images (See Table 1). The volume changes were within 0.5% agreement in this series.

By using end-inspiration and end-exhalation CT scans, the tidal volume was calculated using the regional ventilation algorithm and compared to the volume derived by auto-segmenting the lungs. This tidal volume comparison was performed for the 12 cases (Table 2). The average tidal volume from lung segmentation was 320.1±118.1 cm³, while that from ventilation calculation was 315.9±113.6 cm³. The average difference between the tidal volumes calculated using the two methods was 2.6% and maximum difference was 4.9%.

TABLE 2

| | Case # | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| TV (cm³) by ventilation | 306.8 | 516.4 | 486.6 | 382.2 | 214.2 | 277.8 | 377.1 | 201.4 | 263.9 | 382.1 | 255.5 | 476.2 |
| TV (cm³) by segmentation | 316.6 | 531.5 | 499.3 | 389.0 | 213.6 | 276.4 | 395.6 | 193.5 | 263.1 | 363.5 | 264.2 | 486.1 |
| % difference | −3.2 | −2.9 | −2.6 | −1.8 | 0.3 | 0.5 | −4.9 | 3.9 | 0.3 | 4.9 | −3.4 | −2.1 |

Embodiments of the method and apparatus of the present invention can rely on deformable image registration. The deformation matrices are used to locate the vertexes of a polyhedron in different CT images of respiratory phases and calculate the volume change of the polyhedron between the phases.

Figure 9:
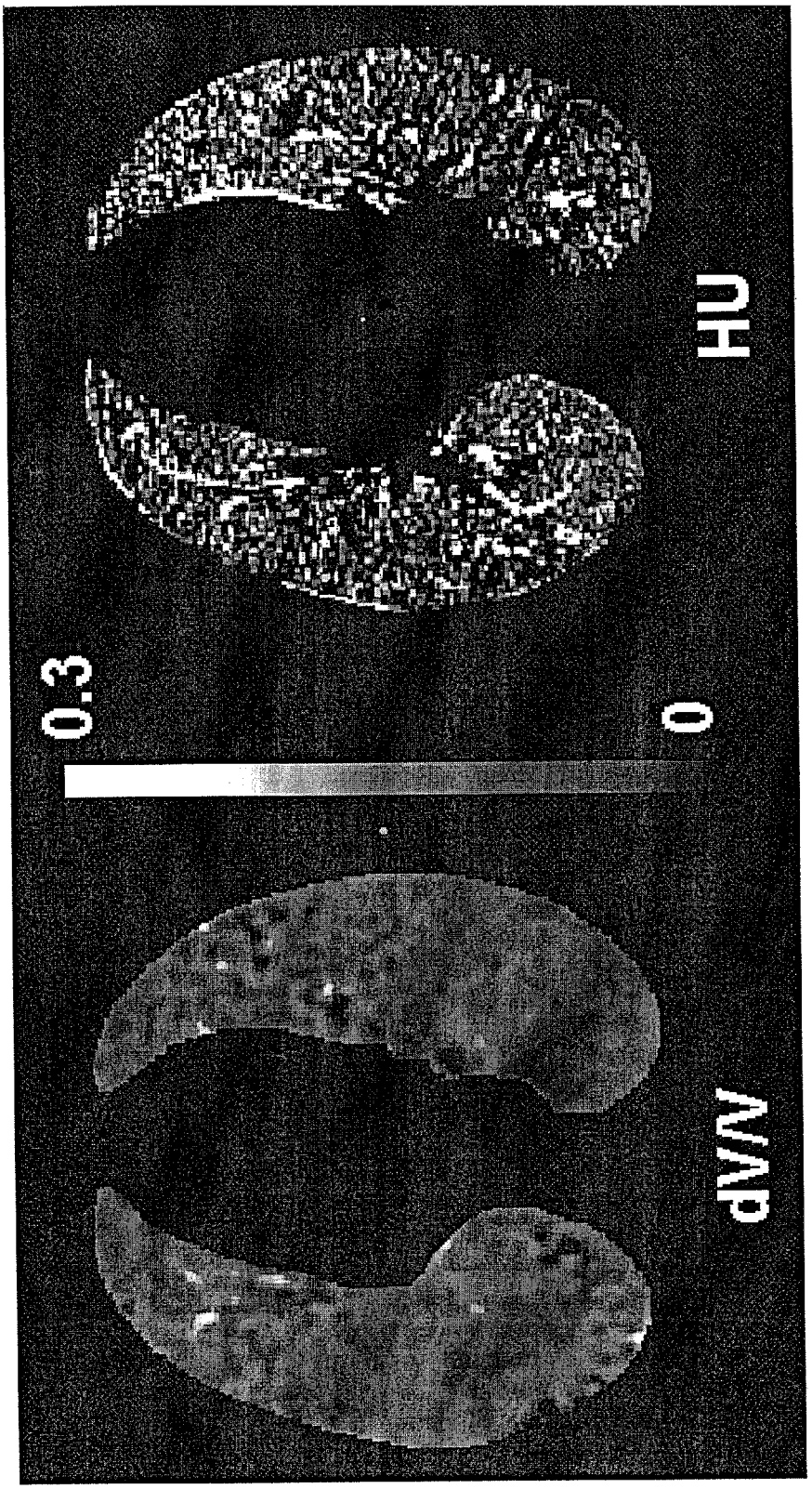
FIG. 9 shows a comparison between the ventilation images using a volume change technique in accordance with an embodiment of the subject invention and a Hounsfield unit (HU) change technique taught by Guerrero T, et al., *Phys Med Biol* 2006; 51:777-791; Guerrero T, et al., *Int J Radiat Oncol Biol Phys* 2005; 62:630-634, where panel A shows the transaxial view of a ventilation image using a volume change technique in accordance with an embodiment of the subject invention and panel B shows an image from the HU change technique at the same slice, where the same 4-D CT data were used for both images and both ventilation images are derived from the maximum expiration (50%) and maximum inspiration (0%) phases.

Embodiments of the method of the present use invention deformable image registration followed by ventilation calculation. The image noise does not have any direct effect in the ventilation calculation. Because of this, the ventilation image using embodiments of the subject invention is less sensitive to image noise and is much smoother than that using the HU change technique. The spatial resolution of the ventilation images thus can be the same as in CT images. FIG. 9 demonstrates the difference between the ventilation images using an embodiment of the subject invention and the HU change-technique. The finest spatial resolution, which is the resolution of the 4-D CT images, is in both images. The embodiment of the subject method gives a much smoother ventilation image than that of the HU change technique. The edge artifact can be seen on the image from the HU change technique. The value ΔV/V=0 (black on the images) means no volume change, ΔV/V=0.3 (white) means volume is increased by 30%.

Noise in the CT images would introduce errors in image registration, which in turn would introduce voxel-to-voxel mismatch. This mismatch would affect the ventilation calculation using either an embodiment of the subject invention or the HU change method, but with a greater effect on the HU change method.

Using larger unit volume in the HU calculation would reduce the magnitude of the errors in the ventilation image. However, it would also introduce a blurring effect which downgrades spatial resolution.

The major source of error of the ventilation imaging in accordance with the subject invention comes from the artifact of 4-D CT images, i.e. the residual motion visible in each respiratory phase. The residual motion in 4-D CT images smears image details and causes registration errors between respiratory phases. The magnitude of the mean error of the registration for the current commercial 4-D CT images using optical flow is sub voxel-size for normal 4-D CT images. (Zhang G, et al., *J Appl Clin Med Phy* 2008; 9:59-69).

Figure 10:
FIG. 10 shows an example of a 4-D CT image with severe motion artifact due to patient movement during the 4-D CT scan, causing a mushroom motion artifact in the coronal view of the 4-D CT images.

Severe motion artifacts in 4-D CT images caused by patient motion, as irregular breathing or large rapid diaphragmatic motion, during CT scan, shown in FIG. 10, would very likely cause the deformable registration to fail, which in turn generates unrealistic ventilation images. As a meaningless defomiation matrix can result from the registration if this series of 4-D CT images is used, the solution to this kind of problem is to retake the 4-D CT images.

The aperture effect (Beauchemin S S, Barron J L, *ACM Computing Surveys (CSUR)* 1995; 27:433-466; Ullman S. The Interpretation of Visual Motion. Cambridge, Mass.: MIT Press; 1979) causes errors when registering volumes of flat intensities. For applications using 4-D human CT images, the errors are most significant in large muscle volumes and fat under skin where few structures are seen in CT images. In the lungs, due to the contrast between the blood vessels and lung tissues, the registration errors display much less in magnitude and frequency than those in the muscles and fat. To reduce aperture effect in the optical flow algorithm, the $2^{nd}$ or even higher order intensity derivatives could be used in the optical flow equations. (Liu H, et al., *Computer Vision and Image Understanding* 1998; 72:271-286). The tradeoff of including higher order derivatives is longer calculation time.

The sharpness of the CT images reduce the aperture effect in the registration. Since breath-hold images usually have better quality with respect to signal-to-noise ratio and motion artifact than in 4-D CT, the ventilation images from breath-hold images should be more accurate than those from 4-D CT images. Improving the quality of 4-D CT images will have a greater effect in improving ventilation imaging than enhancing the deformable image registration algorithm alone. A more accurate deformable registration algorithm aids in reducing errors in the ventilation image.

As 4-D CT is less expensive than nuclear medicine, including SPECT and PET, and easier to perform, all pulmonary ventilation imaging using nuclear medicine could be replaced by this method, unless perfusion imaging is required at the same time. As such, this invention provides substantial benefits for radiological studies for pulmonary fibrosis, emphysema, or other suspicion of reduced lung function. It also provides a practical method for post-therapy evaluation for radiation and chemotherapy patients of thoracic cancers.

Deformable image registration and local volume change calculation provide a practical technique to generate quantifiable pulmonary regional ventilation images from 4-D CT images. The advantages of this algorithm include less sensitive to image noise and mismatch, same spatial resolution in ventilation image as that in CT images. If clinically implemented in radiotherapy treatment planning, it would provide a convenient method to include sparing normal lung volume in planning without additional pulmonary functional imaging procedure and cost.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

It is also to be understood that the following claims are intended to cover all of the generic and specific features of the invention herein described, and all statements of the scope of the invention which, as a matter of language, might be said to fall there between.

What is claimed is:

1. A method of producing a ventilation image, comprising:
    receiving two image data sets, wherein at least a portion of a patient's lung is represented by the two image data sets;
    determining an initial volume, V, for each of a plurality of local volume elements based on a first of the two image data sets;
    calculating a local volume change, $\Delta V$, between the two image data sets for each local volume element;
    calculating $\Delta V/V$ for each local volume element;
    producing a ventilation image having a plurality of ventilation image voxels, wherein each ventilation image voxel corresponds to one or more of the local volume elements and is represented by an indicator corresponding to the one or more $\Delta V/V$ value for the corresponding one or more local volume element.

2. The method according to claim 1, wherein the two image data sets are two computed tomography (CT) image data sets.

3. The method according to claim 1, wherein the first image data set corresponds to a first respiratory phase of the patient and a second image data set of the two image data sets corresponds to a second respiratory phase of the patient.

4. The method according to claim 3, wherein the first respiratory phase is end expiration.

5. The method according to claim 3, wherein the first respiratory phase is end inspiration.

6. The method according to claim 4, wherein the second respiratory phase is end inspiration.

7. The method according to claim 1, wherein each of the two image data sets have a plurality of voxels, wherein each of the plurality of local volume elements corresponds to one of the plurality of voxels of the first image data set.

8. The method according to claim 1, wherein calculating $\Delta V$ comprises:
    applying deformable image registration to the two image data sets so as to create a voxel-to-voxel deformation matrix between the two image data sets; and
    calculating $\Delta V$ from the voxel-to-voxel deformation matrix.

9. The method according to claim 8, wherein each local volume element is represented as a polyhedron.

10. The method according to claim 9, wherein each local volume element is represented as 8 vertices.

11. The method according to claim 9, wherein each local volume element for the first image data set is a cuboid.

12. The method according to claim 10, wherein each polyhedron is a hexahedron.

13. The method according to claim 11, wherein each cuboid is a first hexahedron, wherein each local volume element in the second image data set is represented as a second polyhedron, wherein each second polyhedron has the same 8 vertices as the first hexahedron representing the local volume element in the first image data set, wherein calculating $\Delta V$ for each local volume element comprises calculating a sum of the changes in volume of 6 tetrahedrons that form the first and second polyhedrons.

14. The method according to claim 13, wherein the volume of each tetrahedron is calculated using $$V = (b-a) \cdot [(c-a) \times (d-a)]/6$$

where a, b, c, and d are the vertices of the tetrahedron as vectors.

15. The method according to claim 1, wherein the ventilation image is a 3D ventilation image.

16. The method according to claim 7, wherein each voxel has a volume less than or equal to 3 mm$^3$.

17. The method according to claim 1, wherein each ventilation image voxel corresponds to one of the local volume elements.

18. The method according to claim 1, wherein the indicator is a grayscale indicator.

19. A method of producing a ventilation image, comprising:
    receiving m image data sets, wherein at least a portion of a patient's lung is represented by the m image data sets, wherein m is an integer greater than 2;
    determining an initial volume, V, for each of a plurality of local volume elements based on a first of the m image data sets;
    calculating a first local volume change, $(\Delta V)_1$, between the first image data set and a second of the m image data sets for each local volume element;
    calculating an n$^{th}$ local volume change, $(\Delta V)_n$, between an $(n+1)^{th}$ image data set and an n$^{th}$ image mage data set for each local volume element, for n=2, ..., m−1;
    calculating $(\Delta V)_n/V$ for each local volume element, for n=1, ..., m−1;
    summing $(\Delta V)_n/V$ for n=1, ..., m−1 to produce $(\Delta V)_{sum}/V$;
    producing a ventilation image having a plurality of ventilate image voxels, wherein each ventilation image voxel corresponds to one or more of the local volume elements and is represented by an indicator corresponding to the one or more $(\Delta V)_{sum}/V$ value for the corresponding one or more local volume element.

20. The method according to claim 19, wherein the $(n+1)^{th}$ image data set corresponds to a later phase in the respiratory cycle than the n$^{th}$ image data set.

21. The method according to claim 20, wherein the m image data sets are all from a single respiratory cycle of the patient.

22. The method according to claim 19, wherein the m image data sets are m computed tomography (CT) image data sets.

23. A method for assessing pulmonary function of a patient, comprising producing a ventilation image, wherein producing the ventilation image comprises:
    receiving two image data sets, wherein at least a portion of a patient's lung is represented by the two image data sets;
    determining an initial volume, V, for each of a plurality of local volume elements based on a first of the two image data sets;
    calculating a local volume change, $\Delta V$, between the two image data sets for each local volume element;
    calculating $\Delta V/V$ for each local volume element;
    producing a ventilation image having a plurality of voxels, wherein each ventilation image voxel corresponds to one or more of the local volume elements and is represented by an indicator corresponding to the one or more $\Delta V/V$ value for the corresponding one or more local volume element; and
    assessing pulmonary function of the patient based on the ventilation image.

24. A method for assessing pulmonary function of a patient, comprising producing a ventilation image, wherein producing the ventilation image comprises:

receiving m image data sets, wherein at least a portion of a patient's lung is represented by the m image data sets, wherein m is an integer greater than 2;

determining an initial volume, V, for each of a plurality of local volume elements based on a first of the m image data sets;

calculating a first local volume change, $(\Delta V)_1$, between the first image data set and a second of the m image data sets for each local volume element;

calculating an $n^{th}$ local volume change, $(\Delta V)_n$, between an $(n+1)^{th}$ image data set and an $n^{th}$ image data set for each local volume element, for n=2, ... m−1;

calculating $(\Delta V)_n/V$ for each local volume element, for n=1, ..., m−1;

summing $(\Delta V)_n/V$ for n=1, ..., m−1 to produce $(\Delta V)_{sum}/V$;

producing a ventilation image having a plurality of voxels, wherein each ventilation image voxel corresponds to one or more of the local volume elements and is represented by an indicator corresponding to the one or more $(\Delta V)_{sum}/V$ value for the corresponding one or more local volume element; and assessing pulmonary function of the patient based on the ventilation image.

25. One or more non-transitory computer readable media having computer-usable instructions embodied thereon for performing a method of producing a ventilation image, comprising:

receiving two image data sets, wherein at least a portion of a patient's lung is represented by the two image data sets;

determining an initial volume, V, for each of a plurality of local volume elements based on a first of the two image data sets;

calculating a local volume change, $\Delta V$, between the two image data sets for each local volume element;

calculating $\Delta V/V$ for each local volume element;

producing a ventilation image having a plurality of voxels, wherein each ventilation image voxel corresponds to one or more of the local volume elements and is represented by an indicator corresponding to the one or more $\Delta V/V$ value for the corresponding one or more local volume element.

* * * * *

UNITED STATES PATENT AND TRADEMARK OFFICE
CERTIFICATE OF CORRECTION

PATENT NO.        : 8,538,111 B2
APPLICATION NO.   : 12/988773
DATED             : September 17, 2013
INVENTOR(S)       : Geoffrey G. Zhang et al.

Page 1 of 1

It is certified that error appears in the above-identified patent and that said Letters Patent is hereby corrected as shown below:

In the Specification

Column 5,
Line 50, "$P\Delta V/V$    (2)" should read --$P = \Delta V/V$    (2)--.

Signed and Sealed this
First Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,538,111 B2
APPLICATION NO. : 12/988773
DATED : September 17, 2013
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 260 days.

Signed and Sealed this
Fifteenth Day of September, 2015

Michelle K. Lee
*Director of the United States Patent and Trademark Office*